(12) United States Patent
Khurshid et al.

(10) Patent No.: US 12,178,414 B1
(45) Date of Patent: Dec. 31, 2024

(54) GINGIVAL CREVICULAR FLUID ABSORBING BRUSH

(71) Applicant: King Faisal University, Al-Ahsa (SA)

(72) Inventors: Zohaib Khurshid, Al-Ahsa (SA); Syed Akhtar Bokhari, Al-Ahsa (SA); Muhammad Sohail Zafar, Ajman (AE); Syed Faraz Moin, Karachi (PK); Shariq Najeeb, Ottawa (CA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/661,927

(22) Filed: May 13, 2024

Related U.S. Application Data

(62) Division of application No. 18/229,971, filed on Aug. 3, 2023, now Pat. No. 12,082,788.

(51) Int. Cl.
*A61B 5/00* (2006.01)
*A61B 10/00* (2006.01)

(52) U.S. Cl.
CPC ................ *A61B 10/0045* (2013.01)

(58) Field of Classification Search
CPC ................ A61B 10/0045
See application file for complete search history.

(56) References Cited

U.S. PATENT DOCUMENTS

| | | | |
|---|---|---|---|
| 5,158,871 A | 10/1992 | Rossomando et al. | |
| 5,275,161 A * | 1/1994 | Graves | A61B 5/4547 600/345 |
| 5,628,312 A * | 5/1997 | Musinski | A61C 19/043 600/395 |
| 8,114,027 B2 * | 2/2012 | Triva | C12M 33/02 600/573 |
| 8,631,715 B2 * | 1/2014 | Triva | B01L 3/5029 73/864 |
| 9,170,177 B2 * | 10/2015 | Triva | A61B 10/02 |
| 11,564,777 B2 | 1/2023 | Kopelman et al. | |
| 2003/0120180 A1 * | 6/2003 | Kaylor | A61B 42/00 600/584 |
| 2009/0030341 A1 * | 1/2009 | Kshirsagar | C12M 33/02 600/572 |
| 2009/0030342 A1 * | 1/2009 | Flanigan | B01L 3/5029 600/572 |
| 2009/0298005 A1 * | 12/2009 | Gibbs | A61C 19/043 433/29 |
| 2010/0274155 A1 * | 10/2010 | Battrell | B01L 3/502715 600/572 |
| 2011/0065060 A1 * | 3/2011 | Teixeira | A61C 7/00 433/90 |
| 2011/0082354 A1 | 4/2011 | Ohnishi | |

(Continued)

*Primary Examiner* — May A Abouelela
(74) *Attorney, Agent, or Firm* — Nath, Goldberg & Meyer; Joshua B. Goldberg

(57) ABSTRACT

An instrument and method for collecting and harvesting gingival crevicular fluid samples in a noninvasive manner is provided. Once optimally positioned, an absorbing brush of the instrument is inserted into the gingival sulcus of a patient and held in place while the bristles of the absorbing brush absorb the gingival crevicular fluid. Once removed from the collection sight, the absorbing brush bristles can provide a visual indication of the presence of biomarkers and proteins associated with periodontitis.

8 Claims, 1 Drawing Sheet

(56) References Cited

U.S. PATENT DOCUMENTS

| | | | |
|---|---|---|---|
| 2012/0309042 A1* | 12/2012 | Gittins | G01N 33/525 435/23 |
| 2013/0116596 A1* | 5/2013 | Birnboim | A61B 10/0096 600/572 |
| 2013/0269128 A1* | 10/2013 | Jimenez | A61C 17/3481 15/22.1 |
| 2013/0340185 A1* | 12/2013 | Patel | A61C 15/00 15/104.93 |
| 2014/0323836 A1* | 10/2014 | Kusukame | A61B 5/00 600/300 |
| 2014/0335534 A1* | 11/2014 | Li | G16B 20/20 435/6.15 |
| 2016/0055296 A1* | 2/2016 | Li | C12Q 1/689 702/19 |
| 2016/0327557 A1* | 11/2016 | Haught | G01N 33/5041 |
| 2017/0037450 A1 | 2/2017 | Zourob | |
| 2018/0003598 A1* | 1/2018 | Xie | A61B 10/02 |
| 2018/0317644 A1* | 11/2018 | Xi | A46D 1/023 |
| 2018/0368961 A1* | 12/2018 | Shanjani | A61B 5/4547 |
| 2019/0072560 A1 | 3/2019 | Penman et al. | |
| 2019/0104837 A1* | 4/2019 | Edwards | A61C 17/221 |
| 2019/0176144 A1 | 6/2019 | Thorne et al. | |
| 2020/0172961 A1* | 6/2020 | Wu | C12Q 1/689 |
| 2020/0237091 A1* | 7/2020 | Townsend | A61B 17/244 |
| 2020/0399639 A1 | 12/2020 | Xie et al. | |
| 2021/0022840 A1* | 1/2021 | Deane | A61C 19/04 |
| 2021/0112965 A1* | 4/2021 | Jeanne | G16H 50/30 |
| 2021/0267733 A1* | 9/2021 | Benetti | A61C 17/221 |
| 2021/0393026 A1* | 12/2021 | Subhash | G06T 7/248 |
| 2021/0401408 A1* | 12/2021 | Holcombe | C12Q 1/689 |
| 2022/0087800 A1* | 3/2022 | Wolgin | A61C 19/063 |
| 2022/0275421 A1* | 9/2022 | Ishihara | C12Q 1/37 |
| 2023/0073125 A1* | 3/2023 | Hasani-Sadrabadi | A61K 47/34 |
| 2023/0076737 A1* | 3/2023 | Chen | G01N 33/6863 |
| 2023/0172762 A1* | 6/2023 | Chiarin | A61F 13/38 604/1 |
| 2023/0225715 A1* | 7/2023 | Cobb | B01L 3/52 422/68.1 |
| 2023/0257833 A1* | 8/2023 | Chun | A61B 10/0051 435/5 |
| 2023/0363744 A1* | 11/2023 | Goh | A61B 10/0051 |
| 2023/0363745 A1* | 11/2023 | Goh | C12M 1/30 |
| 2023/0386661 A1* | 11/2023 | Wallis | G16B 10/00 |

\* cited by examiner

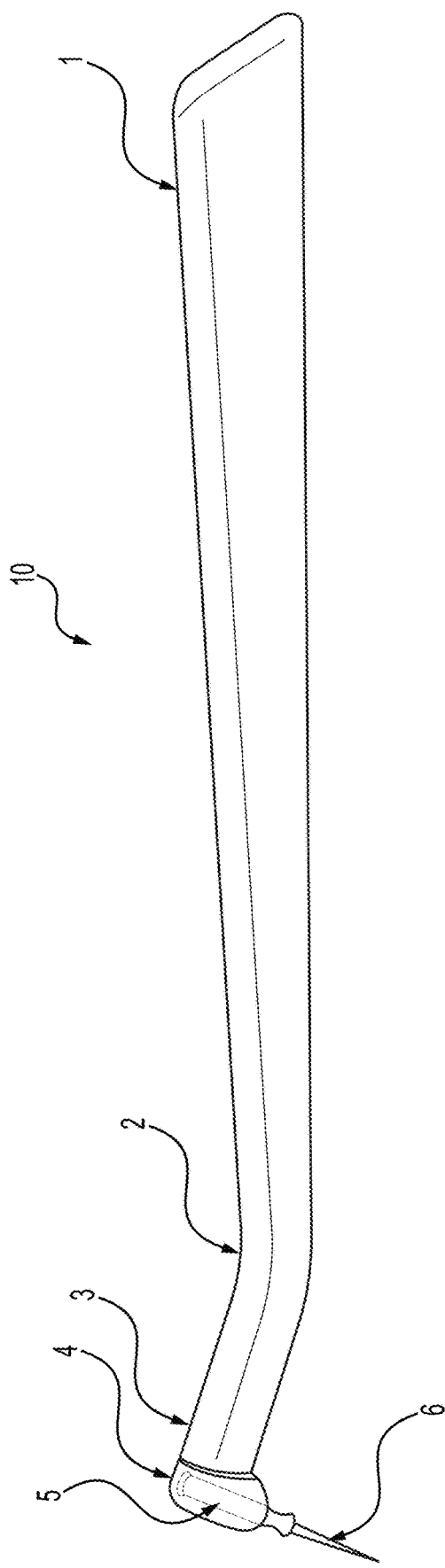

GINGIVAL CREVICULAR FLUID ABSORBING BRUSH

CROSS-REFERENCE TO RELATED APPLICATION

This application is a divisional of U.S. patent application Ser. No. 18/229,971, filed on Aug. 3, 2023, the entire contents of which are incorporated herein by reference.

BACKGROUND

1. Field

The present disclosure relates to a probe for detecting a substance in the body and is useful as an instrument for detecting a substance in the body, more particularly, in gingival crevicular fluid. Specifically, the present disclosure is concerned with a probe for detecting a substance in the body using visual detection of a substance in gingival crevicular fluid.

2. Description of the Related Art

For the detection of a substance in the body, it is generally a widespread practice to collect blood and then optically or electrically analyze the substance in the blood. However, the collection of blood is an invasive method, needs medical qualifications and the like for a phlebotomist, and moreover, is costly. Furthermore, purification of the blood is needed in actual detection or measurement, thereby involving a problem in that additional labor and time are needed to obtain the detection or measurements results. In addition, continuous measurement requires an increased sampling number, so a substantial burden is imposed on the subject being tested. Another problem is that no real-time measurement is feasible.

Therefore, a variety of methods have been developed in recent years to reduce the invasiveness to the body. Taking as an example the measurement of blood sugar levels, non-invasive and low-invasive measuring techniques include a method that is applied to the dermis, arm, fingertip or the like and determines the glucose level in blood by measuring a scattering transmission spectrum with infrared light, a method that is applied to the labial mucosa like and determines the glucose level in blood by measuring a scattering transmission spectrum with infrared light, a method that is applied to the fingertip and like and determines the glucose level in blood by measuring a Raman scattering spectrum, and a method that determines the glucose level in blood by performing a photoacoustic measurement.

On the other hand, the low-invasive measuring methods include a method that measures the glucose level in bodily fluid (intercellular fluid) by collecting bodily fluid from the arm on the same principle of iontophoresis, a method that measures the glucose level in the bodily fluid by collecting the bodily fluid from the skin under ultrasonic waves, a method that measures the glucose level in bodily fluid by collecting the bodily fluid from the arm with a patch or cannula, a method that measures the glucose level in lacrimal fluid by collecting the lacrimal fluid from the eye and conducting holographic diffraction, a method that measures glucose level in saliva by collecting saliva from the mouth, and a method that measures the glucose level in urine by collecting urine samples. However, these low-invasive measuring methods are also accompanied by problems in that they cannot be practiced with the expectation of real-time measurement because glucose levels in the bodily fluid is delayed by 30 minutes or so when compared with the corresponding glucose levels in the blood. As a result, obtaining accurate measurements of the concentration of glucose is problematic because the concentration of the glucose in bodily fluid, lacrimal fluid, saliva, or urine is as low as much as $1/10$th or less than the concentration of glucose in blood.

In the meantime, a method has been under development as a completely noninvasive measuring method to detect a substance in the body where the substance is gingival crevicular fluid (GCF). GCF is an essential biological fluid which is secreted by healthy and diseased gums as a defense mechanism. GCF is rich in proteins and biomarkers which contain genetic, biochemical, and microbial information. Periodontitis, a serious gum infection, can cause tooth loss, and other potentially fatal medical conditions. The variability of periodontal disease genetics, patterning, activity, and treatment response has hampered the accurate and consistent identification of periodontal tissue infection. For this, proper monitoring is required. The amount of GCF is impacted by mechanical variables, environment and habits, circadian periodicity, and the like. The GCF biomarkers may be used to gauge the extent of periodontal disease and to find periodontal bacteria as a sign of an active disease. Currently methods for collecting or harvesting GCF prove to be challenging because of the size limitations of a narrow periodontal pocket GCF collection site and the fact that each collection attempt usually yields insufficient amounts of GCF.

What is needed is a method and device which can easily and effectively collect or harvest the GCF samples from a body in a noninvasive manner and provide a timely visual indication of the presence of the biomarkers and proteins associated with periodontal disease.

SUMMARY

The present invention is directed towards a method and device for collecting or harvesting GCF from a body in order to determine the presence of biomarkers and proteins commonly associated with periodontitis.

In a first aspect of the invention, a device for collecting or harvesting GCF from the gingival sulcus is provided. The device is a hand-held implement that is deployed in the oral cavity where a distal sensing end is inserted in the gingival sulcus where the GCF is detected and absorbed by the distal sensitive end of the hand-held implement. Once a desired amount of GCF has been absorbed, the hand-held implement is retracted from the gingival sulcus and removed from the oral cavity. The distal sensing end is removed from the hand-held implement and placed in a container for storage and cataloging and can be replaced by a new distal sensing end. The sensing ends are contemplated as being insertable and replaceable components such that a multitude of GCF samples can be collected and harvested. The container for storage and cataloging preferably contains a buffer for stabilizing the GCF proteins and biomarkers for subsequent transportation to a laboratory or medical facility for further analysis.

A second aspect of the invention is the method which, when implemented with the device performs the function of collecting or harvesting GCF from a periodontal pocket in order to determine the presence of biomarkers and proteins commonly associated with periodontitis.

These and other features of the present subject matter will become readily apparent upon further review of the following specification.

BRIEF DESCRIPTION OF THE DRAWINGS

FIG. 1 is a diagram of the hand-held implement for collecting and harvesting GCF samples.

Similar reference characters denote corresponding features consistently throughout the attached drawings.

DETAILED DESCRIPTION OF EMBODIMENTS

The following detailed description is merely exemplary in nature and is not intended to limit the described embodiments or the application and uses of the described embodiments. Any implementation described herein with the words "exemplary" or "illustrative" is not necessarily construed as preferred or advantageous over other implementations. All the implementations described below are exemplary implementations provided to enable persons skilled in the art to make or use the embodiments of the disclosure and are not intended to limit the scope of the disclosure, which is defined by the claims. For the purposes of the description herein, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed therein are not to be considered as limiting, unless the claims expressly state otherwise.

FIG. 1 depicts a side-view of the hand-held implement (10) for collecting and harvesting GCF samples from the gingival sulcus of a body. It consists of multiple sections including a main horizontal segment (1) with an inclined handle, an inclined segment (3), a head (4), an absorbing brush holder or cartridge (5), and an absorbing brush (6). The hand-held implement (10) consists of the two main portions: the main horizontal segment (1), and the inclined segment (3) where the inclined segment angles away from main horizontal segment (1) at an end (2) of main horizontal segment (1).

In use, personnel performing the collecting and harvesting will grasp the hand-held instrument (10) by the inclined handle of the main horizontal segment (1), the inclined handle being at the end away from the head (4) and place a distal end of the hand-held instrument (10) including the head (4), absorbing brush holder (5), and absorbing pad/cotton/brush (6) within the oral cavity of the patient. The personnel will then position the distal end of the hand-held instrument (10) such that the absorbing brush (6) is inserted into the gingival sulcus of the patient and held in place while the absorbing brush absorbs the gingival crevicular fluid (GCF) located in the gingival sulcus. The absorbing brush has a generally conical shape and consists of a plurality of specialized cotton fiber bristles which absorb the GCF sample and change color in the presence of the collected and detected biomarkers associated with periodontitis. In particular, the specially treated cotton bristles are made of cotton fibers which change to a red color easily visible to the naked eye. This gives the personnel on-site a real-time assessment as to the presence of periodontic disease. The head (4) has a small opening commensurate in size with the circumference of the absorbing brush holder (5) and thus the absorbing brush holder (5) recently used to collect the GCF sample can be removed from the small opening on the head (4) of the hand-held instrument (10) such that the specially treated cotton bristles can be further analyzed at a remote lab or other facility for a more in depth indication of the extent of the periodontitis associated with the proteins and biomarkers contained within collected or harvested GCF sample. It is noted that the use of the specially treated cotton bristles allows for a quick and unambiguous indication of the presence of periodontitis. The removed absorbing brush holder and absorbing brush can be placed in a special container for convenient transport to the remote lab or other facility. Additionally, the special container also includes a buffer to help stabilize the collected GCF proteins and biomarkers while in transit to the remote lab or other facility for additional study.

It is to be understood that the method and device collecting or harvesting GCF from the gingival sulcus is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for collecting or harvesting a Gingival Crevicular Fluid (GCF) sample from a gingival sulcus of a patient, comprising:
    inserting a new absorbing brush holder into a head of a hand-held instrument;
    grasping an inclined handle which terminates in a main horizontal segment of said hand-held instrument;
    positioning an inclined segment of said hand-held instrument within an oral cavity of said patient, said inclined segment being adjacent to said main horizontal segment at an end opposite said inclined handle;
    positioning said head of said hand-held instrument such that an absorbing brush is inserted into said gingival sulcus of said patient;
    holding said head of said hand-held instrument in place such that said absorbing brush absorbs said GCF sample resident within said gingival sulcus;
    retracting said head of said hand-held instrument such that said absorbing brush exits said gingival sulcus of said patient;
    removing said inclined segment from said oral cavity of said patient;
    detecting a visual indication in said absorbing brush of a presence of biomarkers or proteins associated with periodontitis; and
    removing said absorbing brush holder from said head of said hand-held instrument and placing said absorbing brush holder in a container.

2. The method for collecting or harvesting said GCF sample from said gingival sulcus of said patient as recited in claim 1, wherein said head has an opening commensurate in size with a size of said absorbing brush holder such that said absorbing brush holder is insertable into said opening of said head.

3. The method for collecting or harvesting said GCF sample from said gingival sulcus of said patient as recited in claim 2, wherein said absorbing brush has a conical shape and is made of plurality of bristles.

4. The method for collecting or harvesting said GCF sample from said gingival sulcus of said patient as recited in claim 3, wherein said plurality of bristles are made of specially treated cotton fibers.

5. The method for collecting or harvesting said GCF sample from said gingival sulcus of said patient as recited in claim 4, wherein said visual indication is when said plurality of bristles change to a visible red color when said presence of said biomarkers and said proteins associated with said periodontitis are detected.

6. The method for collecting or harvesting said GCF sample from said gingival sulcus of said patient as recited in claim 5, wherein said container further includes a buffer to stabilize said biomarkers and said proteins.

7. The method for collecting or harvesting said GCF sample from said gingival sulcus of said patient as recited in claim 6, wherein said plurality of bristles are made of said specially treated cotton fibers.

8. The method for collecting or harvesting said GCF sample from said gingival sulcus of said patient as recited in claim 7, wherein said plurality of bristles change to said visible red color when said presence of said biomarkers and said proteins associated with said periodontitis are detected.

* * * * *